United States Patent [19]

Collins

[11] 4,378,794

[45] Apr. 5, 1983

[54] SURGICAL DRAPE

[75] Inventor: Robert F. Collins, Barrington, Ill.

[73] Assignee: The Kendall Company, Boston, Mass.

[21] Appl. No.: 223,189

[22] Filed: Jan. 7, 1981

[51] Int. Cl.³ .............................................. A61F 13/00
[52] U.S. Cl. ................................................ 128/132 D
[58] Field of Search ............................ 128/132 D, 292

[56] References Cited

U.S. PATENT DOCUMENTS 3,791,382  2/1974  Collins ............................ 128/132 D
4,059,104 11/1977  DePriest et al. ................ 128/132 D
4,169,472 10/1979  Morris ............................. 128/132 D Primary Examiner—C. Fred Rosenbaum
Attorney, Agent, or Firm—Powell L. Sprunger

[57] ABSTRACT

A surgical drape comprising, a main sheet of flexible material having a fenestration, and an opening in the expected path of fluid runoff from the fenestration. The drape has a fluid pervious screen covering the opening. The drape also has a pocket comprising a flap covering a lower portion of the screen, with the flap having an upper edge and defining a cavity facing toward the expected path of fluid runoff from the fenestration.

7 Claims, 4 Drawing Figures

SURGICAL DRAPE

BACKGROUND OF THE INVENTION

The present invention relates to surgical drapes.

During certain cystoscopy procedures, particularly the surgical procedure of transurethral resection of the prostate gland, large amounts of water are used to flush the site of surgery. Although surgical drapes with a built-in filter screen have been provided to dispose of water to the hospital plumbing system, much of the water overflows onto the floor and onto the urologist who sits adjacent the drape and patient. Also, tissue fragments, which are shaved from the prostate gland during the procedure, should be saved for analysis by the pathologist. However, many of these particles are lost, since they are washed away with the overflowing water.

SUMMARY OF THE INVENTION

A principal feature of the present invention is the provision of an improved surgical drape of simplified construction.

The surgical drape of the present invention comprises, a main sheet of flexible material having a fenestration, and an opening in the expected path of fluid runoff from the fenestration. The drape has a fluid pervious screen covering the opening. The drape also has a pocket comprising a flap covering a lower portion of the screen, with the flap having an upper edge and defining a cavity facing toward the expected path of fluid runoff from the fenestration.

A feature of the present invention is that the flap controls the fluid runoff from the fenestration, and directs it toward the screen for disposal.

Another feature of the present invention is that the flap prevents the overflow of fluid runoff from the screen.

Yet another feature of the invention is that the flap prevents the escape of tissue shavings, and directs them for retention on the screen.

Further features will become more fully apparent in the following description of the embodiments of this invention and from the appended claims.

DESCRIPTION OF THE PREFERRED EMBODIMENTS

Figure 1:
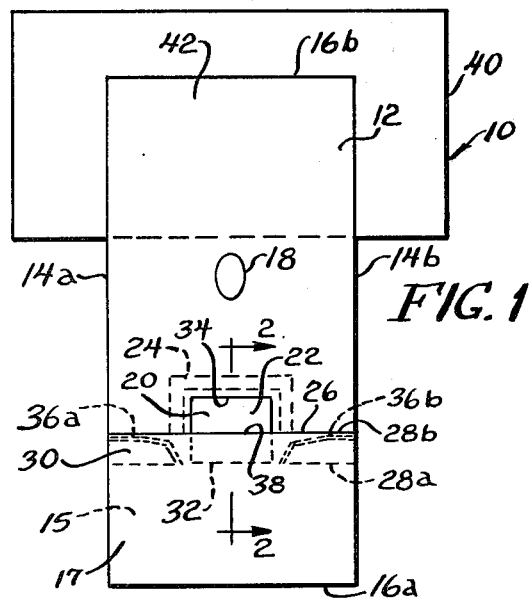
FIG. 1 is a front plan view of a surgical drape of the present invention.
Figure 2:
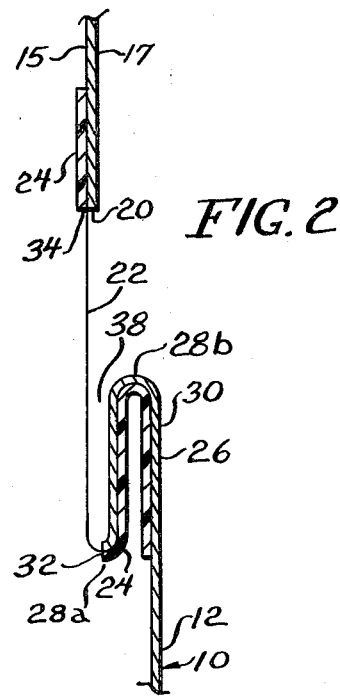
FIG. 2 is a fragmentary sectional view taken substantially as indicated along the line 2—2 of FIG. 1.
Figure 3:
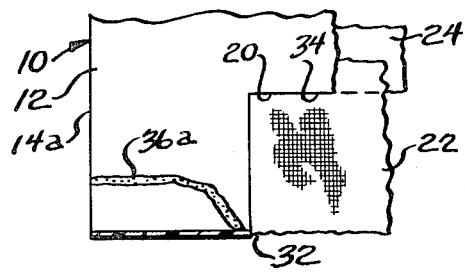
FIG. 3 is a front plan view, partly broken away, of a portion of the drape of FIG. 1.

Referring now to FIGS. 1-3, there is shown a surgical drape generally designated 10 having a main sheet 12 of flexible material, such as a nonwoven material. The main sheet 12 has a pair of generally aligned side edges 14a and 14b, a pair of generally aligned end edges 16a and 16b connecting the side edges 14a and b, a lower surface 15 facing toward the patient after placement of the drape, and an upper surface 17 facing away from the patient after placement of the drape. The main sheet 12 has a fenestration 18, and a generally rectangular opening 20 intermediate the fenestration 18 and the end edge 16a of the main sheet 12, and positioned in the expected path of fluid runoff from the fenestration 18 during a surgical procedure.

The drape 10 has a screen 22, such as a nylon screen, a cotton mesh, or perforated plastic material, extending across and covering the opening 20 in the main sheet 12. The drape 10 has a reinforcement sheet 24 of flexible material, such as a suitable plastic material, extending peripherally around the edges of the opening 20, with the reinforcement sheet 24 being secured by suitable means, such as by adhesive, to the main sheet 12, and with outer edges of the screen 22 being secured to the drape 10 intermediate the reinforcement sheet 24 and the main sheet 12.

The drape 10 has a pocket 26 comprising a pair of transverse spaced and aligned fold lines 28a and 28b in the main sheet 12 which extend between the side edges 14a and b of the main sheet 12, and which define a flap 30 which overlies a lower portion of the opening 20. As shown, the fold line 28a defines a lower portion of the flap 30, and the fold line 28b defines an upper or outer edge of the flap 30. In a preferred form, a lower edge 32 of the opening 20 is located adjacent the fold line 28a of the flap 30, while an upper edge 34 of the opening 20 is located intermediate the outer edge 28b of the flap 30 and the fenestration 18. The flap 30 is secured to the underlying portion of the main sheet 12 by a pair of seal lines 36a and 36b on opposed sides of the opening 20, such as lines of adhesive, which taper from the outer edge 28b of the flap 30 toward the lower portion of the flap 30 adjacent the lower edge 32 of the opening 20. In this configuration, the secured flap 30 defines a cavity 38 which faces toward the fenestration 18 in the expected path of fluid runoff from the fenestration 18.

In a preferred form, the drape 10 has a second main sheet 40 of flexible material, such as a nonwoven material, secured to an upper portion 42 of the drape 10 intermediate the fenestration 18 and the end edge 16b of the main sheet 12. As shown, the second main sheet 40 extends past the side edges 14a and b of the main sheet 12.

Figure 4:
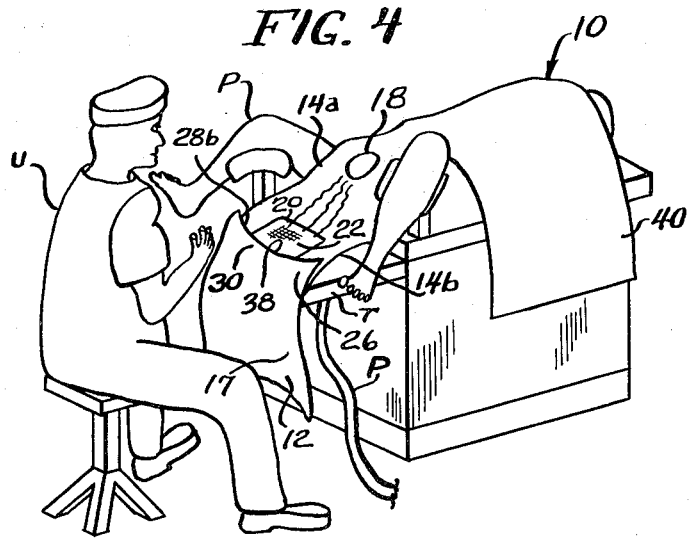
FIG. 4 is a perspective view showing the drape as positioned for use on a patient.

In use, with reference to FIG. 4, a patient P is placed upon a suitable operating table, and the drape 10 is placed over the patient P, with the second main sheet 40 covering an abdominal portion of the patient P, and with the main sheet 12 extending between the patient's legs. In this configuration, the screen 22 is located over a tray T of the table, with the pocket 26 and screen 22 being located below the fenestration 18 in the expected path of fluid runoff from the fenestration 18. During the surgical procedure, large amounts of water are utilized to flush the site of surgery, and the water then passes from the fenestration 18 downwardly along the drape 10 toward the screen 22 and pocket 26. The pocket 26 forms a dam to direct the water toward the screen 22 through which it passes to the tray T of the table and into a pipe P for capture in the hospital plumbing system. Thus, the pocket 26 prevents the overflow of water from the screen 22, while the tapered seal lines 36a and b direct the water toward a lateral central portion of the flap 30 and the lower portion of the screen 22. In this manner, the pocket 26 cooperates with the screen 22 to prevent the overflow of liquid onto the floor and onto the urologist U who sits beside the drape 10 and the table. In addition, the pocket 26 prevents the escape of tissue fragments in the water, and directs them onto the screen 22 for collection on the screen 22 in order that they may be accumulated for subsequent analysis by a pathologist.

The foregoing detailed description is given for clearness of understanding only, and no unnecessary limitations should be understood therefrom, as modifications will be obvious to those skilled in the art.

I claim:

1. A surgical drape, comprising:

a main sheet of flexible material having a pair of side edges, a pair of end edges connecting said side edges, a fenestration, an opening located intermediate said fenestration and one of said end edges, and a pair of generally aligned fold lines extending between said side edges and defining a flap secured to an underlying portion of the main sheet, with a lower edge of the opening being located adjacent a lower portion of the flap such that the flap overlies a lower portion of the opening, with the flap having an upper edge and defining a cavity facing toward the fenestration, and with an upper portion of the opening being located intermediate the upper edge of the flap and the fenestration; and a fluid pervious screen covering said opening.

2. The drape of claim 1 including a reinforcement sheet extending around said opening, with edges of said screen being located intermediate the main sheet and reinforcement sheet.

3. The drape of claim 1 wherein said opening has a generally rectangular shape.

4. The drape of claim 1 wherein said flap is secured to the main sheet along lines tapering from the upper edge of the flap toward a lower portion of the flap adjacent said opening.

5. The drape of claim 1 wherein said flap is secured to the main sheet along lines tapering from the upper edge of the flap toward a lower portion of said opening.

6. The drape of claim 1 wherein said flap comprises a pair of generally aligned transverse fold lines in said main sheet.

7. The drape of claim 1 wherein said main sheet includes a pair of side edges, and including a second main sheet extending transversely past said side edges on an upper portion of the drape above the fenestration.

* * * * *